(12) United States Patent
Welch et al.

(10) Patent No.: US 7,141,150 B1
(45) Date of Patent: Nov. 28, 2006

(54) METHOD AND TEST CHAMBER FOR ACCELERATED AGING OF MATERIALS AND BONDS SUBJECT TO CORROSION RELATED DEGRADATION

(75) Inventors: John R. Welch, Bourne, MA (US); Thomas S. Ramotowski, Tiverton, RI (US); Gerald J. Roche, Freetown, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 380 days.

(21) Appl. No.: 10/895,469

(22) Filed: Jul. 19, 2004

(51) Int. Cl.
*G01N 27/26* (2006.01)
*C23F 13/00* (2006.01)

(52) U.S. Cl. .................. 204/401; 204/404; 204/196.01; 204/196.06; 204/196.07; 204/196.1; 204/196.21; 204/196.34; 204/196.36

(58) Field of Classification Search ................ 204/401, 204/404, 196.01, 196.06, 196.07, 196.1, 204/196.21, 196.34, 196.36
See application file for complete search history.

(56) References Cited

U.S. PATENT DOCUMENTS

| 3,439,531 | A | | 4/1969 | Sipes |
| 4,282,181 | A | | 8/1981 | Pierce |
| 4,559,824 | A | | 12/1985 | Soma et al. |
| 5,942,333 | A | * | 8/1999 | Arnett et al. ............... 428/469 |
| 6,053,035 | A | | 4/2000 | Nomura et al. |

* cited by examiner

*Primary Examiner*—Bruce F. Bell
(74) *Attorney, Agent, or Firm*—Jean-Paul A. Nasser; James M. Kasischke; Michael P. Stanley

(57) ABSTRACT

A method and test apparatus for carrying out testing on a variety of samples of polymer bonded to metal wherein the samples are subjected to an accelerated cathodic reaction causing cathodic delamination of the samples. In particular, the method and test apparatus include a closed vessel that is partially filled with synthetic ocean water. An impressed current system is employed to protect the metal component of the samples. The synthetic ocean water is heated with an external band heater raising the temperature of the synthetic ocean water to thermal levels exceeding normal ocean temperatures in order to accelerate the reaction. Pure oxygen is then introduced into the closed vessel at a desired pressure to dissolve the oxygen into the synthetic ocean water to further simulate natural ocean conditions.

14 Claims, 2 Drawing Sheets

METHOD AND TEST CHAMBER FOR ACCELERATED AGING OF MATERIALS AND BONDS SUBJECT TO CORROSION RELATED DEGRADATION

The invention described herein may be manufactured and used by or for the Government of the United States of America for governmental purposes without the payment of any royalties thereon or therefore.

CROSS REFERENCE TO OTHER RELATED APPLICATIONS

Not applicable.

BACKGROUND OF THE INVENTION (1) Field of the Invention

The present invention relates to the testing of polymer to metal bonds, and more specifically to a method and apparatus for demonstrating the durability of polymer to metal bonds in a cathodic environment by subjecting samples to accelerated cathode reactions that cause cathodic delamination.

(2) Description of the Prior Art

Polymer to metal bonds are increasingly used in vessels and devices designed for use in marine environments. It is vital that these bonds maintain their integrity while exposed to saltwater. Of particular concern is the problem of cathodic delamination, which occurs when the metal hull of a marine vehicle is protected from corrosion by using a "sacrificial" anode system. In a situation where the anode is made of zinc, the reaction is $2Zn \rightarrow 2ZN^{+2}+4e^-$. The cathodic reaction is $O_2+2H_2O+4e^- \rightarrow 4(OH)^-$. Over a period of several months and years, the hydroxide ions $(OH)^-$ become highly concentrated at the cathode, creating a high alkalinity water environment destructive to polymer to metal bonds. In fact, cathodic delamination is the most commonly encountered failure for polymer to metal bonds in the marine environment.

In order to anticipate which polymer to metal bonds are most resistant to cathodic delamination, it is necessary to test the bonds in artificially created marine conditions. One prior art testing method and apparatus places the polymer to metal bond samples inside an open container filled with synthetic ocean water, and drill holes in the unbonded portion of the metal in order to suspend the samples from an electrically conductive rod. The water is heated using a stainless steel immersion heater. Any evaporated water is replaced with water of an approximate conductivity to the electrolyte contained in the open vessel. The emphasis on this testing method and apparatus is on water temperature based on the theory that the diffusion of water controls the degradation rate of polymers and adhesives and therefore elevated temperatures will increase the rate of water permeation through the polymer thereby artificially accelerating the "aging" of the polymer to metal bond. There is no attention to dissolved oxygen or conductivity in this testing method.

Water, however, is not the only reactant that can affect the degradation rate of a bond. Cathodic delamination will not proceed if there is no dissolved oxygen in the water or if there are no electrons supplied to the cathode. In light of this, other prior art testing method and apparatus use a bubbling system in an attempt to maintain the dissolved oxygen in water at elevated temperatures. Such a system, however, is limited to maintaining the dissolved oxygen level that is physically allowable at the particular elevated water temperature.

There is currently no method and test apparatus to artificially accelerate the effect of cathodic delamination on polymer to metal bonds that also maintains the levels of dissolved oxygen in water and the levels of electrical current that would be encountered in the normal course by marine vehicles when the metal hull of the marine vehicle is protected from corrosion by using a "sacrificial" anode system. What is needed is a method and test apparatus that subjects different polymer to metal bonds to artificially accelerated cathodic delamination under typical marine conditions.

SUMMARY OF THE INVENTION

It is a general purpose and object of the present invention to provide a test chamber wherein polymer to metal bond samples are subjected to artificially accelerated cathodic delamination.

It is another object of the present invention to maintain proper levels of dissolved oxygen in the water in the test chamber at high temperatures.

It is another object of the present invention to use an external band heater to elevate and control the temperature of the test chamber.

It is another object of the present invention to maintain the desired electrochemical potential of each polymer to metal bond sample.

It is another object of the present invention to use an adjustable impressed current system to adjust the power supply to account for the reduction in current as polymer to metal bond samples are removed from the test chamber.

These objects are accomplished with the present invention by providing a closed vessel test chamber that maintains a controlled simulated ocean environment in which polymer to metal bond samples are placed in heated synthetic ocean water. An impressed current is run in the chamber to protect the metal component of the bond samples, and pressurized oxygen is forced into the test chamber to maintain appropriate levels of dissolved oxygen in the heated synthetic ocean water.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
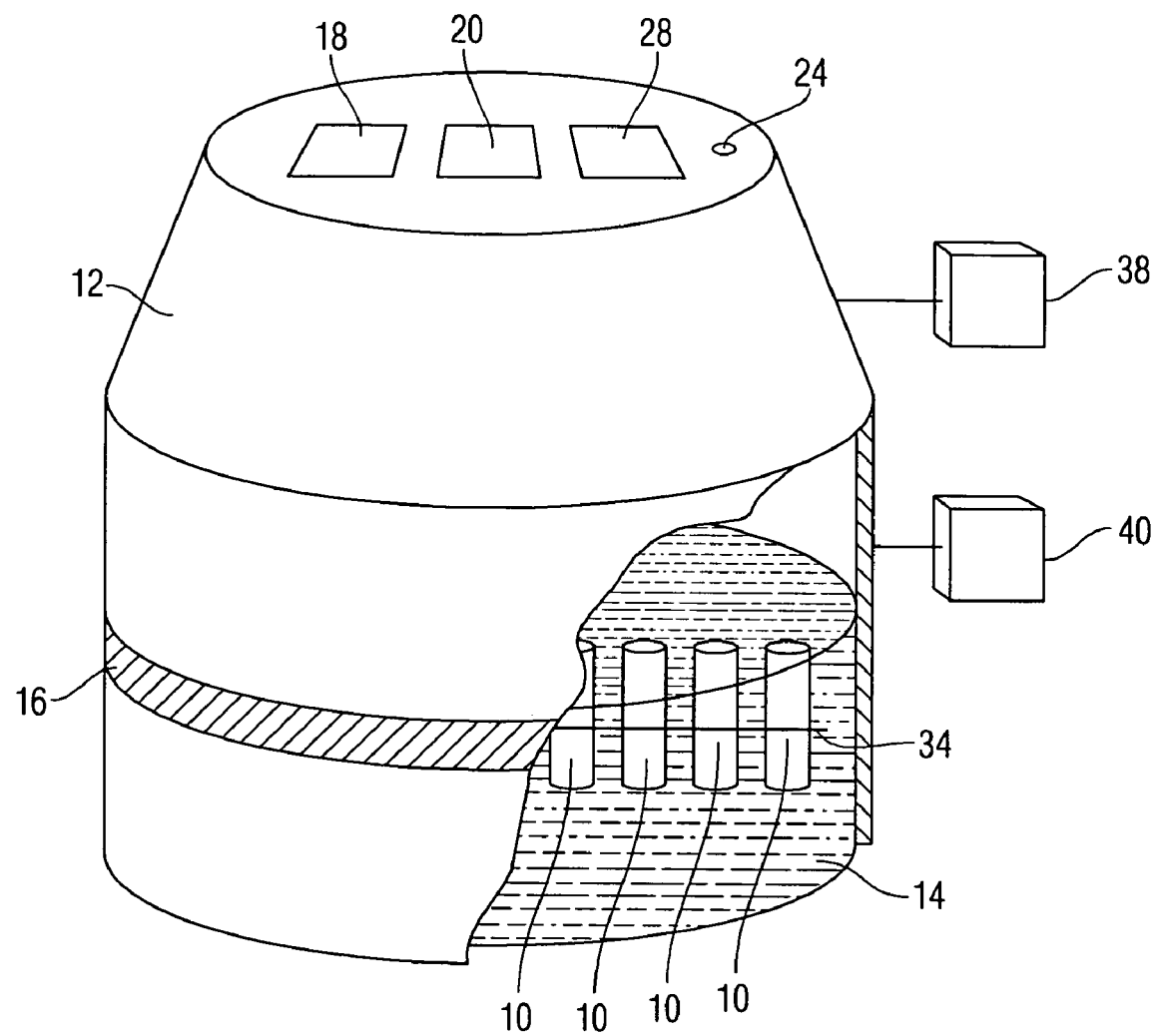
FIG. 1 shows the test chamber where polymer to metal bond samples are placed.

Referring now to FIG. 1 there is shown multiple bonding samples 10. The samples 10 are composed of a polymer bonded to a metal substrate. In the preferred embodiment, all of the samples are of the same dimensions. The samples 10 are placed inside a closed vessel that serves as the test chamber 12. In the preferred embodiment, the test chamber 12 is made of inert materials such as polypropylene, and nylon. The test chamber 12 is partially filled with a fluid designed to approximate certain properties of natural ocean water as closely as possible particularly with regard to salinity, and conductivity at various temperatures and pressures. For example, natural ocean water has an average salinity of 35 ppt at 15° C., 1 atm, and 43 mS/cm. In the preferred embodiment, synthetic ocean water 14 is used to approximate natural ocean water, however the invention is not to be limited by the use of one particular fluid.

The synthetic ocean water 14 is heated using an external band heater 16. By increasing the temperature of the synthetic ocean water 14 in the test chamber 12 the effect of exposure on the bonding samples 10 is artificially accelerated. A thermometer 18 is used to monitor the water temperature.

Figure 2:
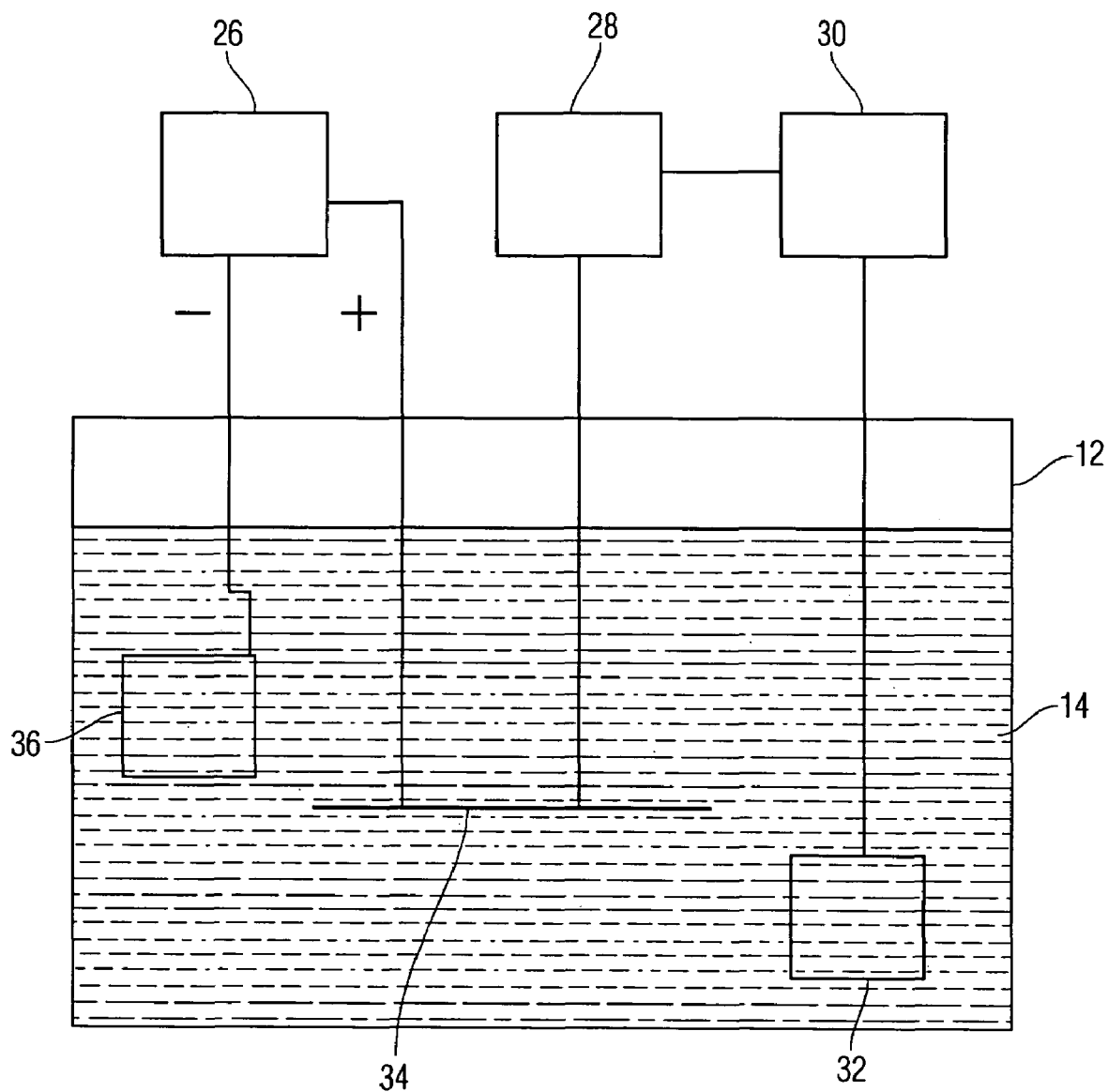
FIG. 2 shows a diagram of the impressed current system in the test chamber.

The metal substrate of each polymer to metal bond sample 10 is cathodically protected using an impressed current system as illustrated in FIG. 2. The impressed current system includes a voltmeter 26 and current meter 28 joined to a power supply 30. A stainless steel plate is used as the anode 32. The power supply 30 removes the electrons from the steel anode 32 to a stainless steel cathode bus line 34. It is to be understood that the invention is not limited to the use of stainless steel for the anode and cathode. The cathode bus line 34 is used to electrically connect several bond samples 10 simultaneously. The cathode bus line 34 is then connected in parallel to maintain all bond samples 10 at a desired electrochemical potential relative to a reference cell 36. In a preferred embodiment, the reference cell 36 is composed of Ag/Ag—Cl, however, any calibrated reference electrode could be used.

In the preferred embodiment, the desired electrochemical potential of each polymer to metal bond sample 10 relative to the reference cell 36 is −0.85 volt which is the voltage normally used to protect a steel hulled marine vessel that might naturally corrode at −0.600 volt. The current used to maintain the cathode bus line 34 at −0.85 volt relative to the reference cell 36 is dependent on the amount of wet surface area requiring cathodic protection. Approximately 10 mA is required to protect one square foot of wetted surface area.

Using an impressed current system requires an adjustment to the power supply 30 to account for the reduction in current as samples are removed from the test chamber 12. A zinc anode system for example would require a complete zinc anode resizing to ensure that the correct amount of current is being supplied to cathodically protect the remaining samples. Supplying too much current to the samples not only may cause an unknown effect in the cathodic delamination reaction, but changes the corrosion rate and also may cause the production of hydrogen gas in specific voltage regimes, which is highly explosive in a closed vessel containing pure oxygen. As more bonding samples 10 are removed from the test chamber 12 the required current will initially drop and then increase as the gradual delamination of the polymer occurs and subsequently there is an increase in metal surface area exposed to the electrolyte.

As the band heater 16 increases the temperature of the synthetic ocean water 14 to artificially accelerate the exposure of the bonding samples 10, the level of dissolved oxygen will drop far below normal levels at lower temperatures. The dissolved oxygen level in 15° C. natural ocean water is approximately 8 ppm. Maintaining this level of dissolved oxygen while at temperatures much higher than 15° C. requires an increase in the partial pressure of oxygen in the atmosphere above the synthetic ocean water 14. A dissolved oxygen sensor 20 is used to measure the amount of dissolved oxygen in the synthetic ocean water 14. The level of dissolved oxygen is maintained at normal ocean temperature conditions (15° C.) by injecting oxygen into the test chamber 12 through the pure oxygen inlet 24. A vacuum pump 38 is used to evacuate all of the air in test chamber 12 after which the pure oxygen is injected into test chamber 12. To accelerate the dissolution of oxygen into the synthetic ocean water 14, a circulation pump 40 is used to create a turbulent mixing surface within test chamber 12. The circulation pump 40 also creates a slight water velocity across the tip of the dissolved oxygen sensor 20. This is necessary to obtain an accurate measurement, because in stagnant water the sensor 20 would completely consume the dissolved oxygen in its immediate surroundings.

Leaving various types of polymer to metal bond samples 10 in the vessel under the appropriate conditions as described above provides a determination as to which polymer to metal bonds are the most resistant to cathodic delamination. The period of test time that the bond samples 10 should be left in the vessel is derived through the use of the Arrhenius Equation which states that $K=Ae^{-E/RT}$, where K=specific reaction velocity (speed of the reaction), E=energy of activation (dependent on the type of reaction), A=constant (frequency factor), R=gas law constant (1.99 calories/degree-mole), T=temperature (absolute), and e=base of the natural logarithm. The reaction acceleration factor (RAF) for reaction velocities K1 and K2 for a given reaction at T1 and T2, where T2>T1, is defined as $RAF=K2/K1=e^{E(T2-T1)/R(T1 T2)}$. The value of RAF is used to obtain the number of test days at the elevated temperature T2 that will simulate 1 year of exposure at T1: Test Time (@T2)=365/RAF. The calculation of test time is highly dependent on the value of the energy activation E. Any inaccuracies in the estimation of the energy activation for the reaction will result in drastic inaccuracies in the calculation of test time. Past studies estimate 13,000 calories/mole as a composite energy of activation for water permeation through various elastomers.

The advantages of the present invention over the prior art are that the use of a closed vessel test chamber provides the ability to manipulate the environment that contains the polymer to metal bond samples 10 by for example creating a pure oxygen atmosphere to maintain appropriate dissolved oxygen levels in the synthetic ocean water 14. Prior art testing devices have ignored the decrease in dissolved oxygen concentration at the higher water temperature level at which a test is normally conducted. Lower than normal concentrations of dissolved oxygen in the synthetic ocean water 14 will actually slow the cathodic delamination reaction, thereby generating "false positive" results that seriously over-estimate the actual resilience of the bond samples 10 to cathodic delamination. Creating an excess of pure oxygen in the atmosphere above the synthetic ocean water 14 in the test chamber 12 ensures that the dissolved oxygen used up by the cathodic delamination reaction during the test is quickly replaced.

Prior art testing methods and apparatus have no provision for replacing the dissolved oxygen used up during a test. Some prior art testing methods and apparatus replace oxygen with forced air, which introduces large amounts of carbon dioxide into the synthetic ocean water 14. Carbon dioxide, which is much more soluble than oxygen in water, will react with water to form carbonic acid. The introduction of excess carbonic acid into the synthetic ocean water 14 will affect the pH of the water. It could also react with the hydroxide ions generated by the cathodic delamination reaction thereby preserving the bond and ultimately compromising the testing.

The use of a closed vessel test chamber also ensures that little or no water is evaporated during the test and that the conductivity of the synthetic ocean water 14 remains constant.

The present invention uses an external band heater 16 to reduce "unknowns" created by adding an additional piece of metal into the test chamber 12 like an immersion heater.

The use of an impressed current system in the present invention rather than a zinc anode provides the ability to adjust the current level used to cathodically protect the metal substrates of the polymer to metal bond samples 10 with out the need of adjusting the size of the zinc anode or replacing it. It also avoids the build up of dissolved zinc in the test chamber 12 which can actually slow the cathodic delamination reaction or even cause it to reverse direction because of Le Chatilier's Principle.

Obviously many modifications and variations of the present invention may become apparent in light of the above teachings. For example: The temperature of the water inside the accelerated life testing chamber can be set to different temperatures to either speed up or slow down the rate of the cathodic delamination reaction. The test chamber can be used to accelerate the aging of systems exposed to a variety of ocean water temperatures. A sodium chloride solution of the proper salinity and chlorine content can be substituted for synthetic ocean water. Sacrificial metal anodes (e.g. zinc) can be substituted for the battery employed in the impressed current system. A variety of different reference electrodes (properly calibrated) can be used to monitor the system. A variety of different metals/alloys can be used as the anode in the impressed current system. The closed vessel that is the test chamber 12 can be scaled up to hold larger size samples or a larger number of smaller samples.

In light of the above, it is therefore understood that within the scope of the appended claims, the invention may be practiced otherwise than as specifically described.

What is claimed is:

1. An apparatus for subjecting a sample of material to cathodic delamination comprising:
    a test chamber for containing the sample of said material;
    a quantity of electrolytic fluid that approximates the properties of ocean water contained in said test chamber in which said sample is immersed;
    a means for controllably heating said electrolytic fluid while said electrolytic fluid is contained in said test chamber;
    a means for dissolving oxygen into said electrolytic fluid while said electrolytic fluid is contained in said test chamber; and
    a means for cathodically protecting said sample while said sample immersed in said electrolytic fluid.

2. The apparatus of claim 1 wherein said quantity of electrolytic fluid that approximates the properties of ocean water comprises synthetic ocean water.

3. The apparatus of claim 1 wherein said means for controllably heating said electrolytic fluid while said electrolytic fluid is contained in said test chamber comprises an external band heater joined to said test chamber.

4. The apparatus of claim 1 wherein said means for dissolving oxygen into said electrolytic fluid while said electrolytic fluid is contained in said test chamber comprises:
    at least one pump joined to said test chamber to remove air from the test chamber, and then force oxygen into the test chamber at variable pressure levels, and then create a turbulent mixing surface within said test chamber.

5. The apparatus of claim 1 wherein said means for cathodically protecting the sample while said sample is immersed in said electrolytic fluid comprises:
    a first metal plate for use as an anode;
    a second metal plate for use as a cathode joined to said sample;
    a voltmeter in electrical contact with said anode;
    a current meter in electrical contact with said anode;
    a reference cell in electrical contact with said cathode; and
    a power supply in electrical contact with said anode and said cathode, said power supply capable of removing the electrons from said first metal plate anode to said second metal plate cathode to maintain said sample of material at a desired electrochemical potential relative to said reference cell.

6. The apparatus of claim 5 wherein said first metal plate is stainless steel.

7. The apparatus of claim 5 wherein said second metal plate is stainless steel.

8. The apparatus of claim 5 wherein said cathode comprises a cathode bus line that electrically connects at least one sample of said material.

9. The apparatus of claim 5 wherein said reference cell is composed of Ag/Ag—Cl.

10. The apparatus of claim 5 wherein said desired electrochemical potential relative to said reference cell is −0.85 volts.

11. The apparatus of claim 1 wherein said test chamber is a closed vessel composed of inert material.

12. The apparatus of claim 11 wherein said inert material is polypropylene, and nylon.

13. The apparatus of claim 1 wherein said sample of material is a polymer bonded to a metal substrate.

14. The apparatus of claim 1 wherein the time that the sample material is tested in said test chamber is derived through the use of the Arrhenius Equation.

* * * * *